United States Patent
Olejnik et al.

(10) Patent No.: US 10,655,171 B2
(45) Date of Patent: *May 19, 2020

(54) MODULAR FLOW CELLS AND METHODS OF SEQUENCING

(71) Applicants: QIAGEN SCIENCES, LLC, Germantown, MD (US); QIAGEN GmbH, Hilden (DE)

(72) Inventors: Jerzy Olejnik, Brookline, MA (US); Dirk Zimmermann, Cham (CH)

(73) Assignees: QIAGEN SCIENCES, LLC, Germantown, MD (US); QIAGEN GmbH, Hilden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/181,918

(22) Filed: Nov. 6, 2018

(65) Prior Publication Data

US 2019/0071722 A1 Mar. 7, 2019

Related U.S. Application Data

(63) Continuation of application No. 15/215,234, filed on Jul. 20, 2016, now Pat. No. 10,150,994.

(60) Provisional application No. 62/195,585, filed on Jul. 22, 2015.

(51) Int. Cl.
*C12Q 1/68* (2018.01)
*C12Q 1/6869* (2018.01)
*C12Q 1/6874* (2018.01)

(52) U.S. Cl.
CPC ......... *C12Q 1/6869* (2013.01); *C12Q 1/6874* (2013.01)

(58) Field of Classification Search
CPC .................................................. C12Q 1/16869
USPC ............................................................ 435/6.1
See application file for complete search history.

(56) References Cited

U.S. PATENT DOCUMENTS

| | | | |
|---|---|---|---|
| 5,547,839 A | 8/1996 | Dower et al. | 435/6 |
| 8,481,259 B2 * | 7/2013 | Gordon | B01L 3/502761 435/6.1 |
| 8,612,161 B2 | 12/2013 | Gordon et al. | 702/20 |
| 8,900,810 B2 * | 12/2014 | Gordon | B01L 3/502761 435/6.1 |
| 10,150,994 B2 * | 12/2018 | Olejnik | C12Q 1/6869 |
| 2002/0025529 A1 | 2/2002 | Quake et al. | 422/99 |
| 2010/0330569 A1 | 12/2010 | Olejnik | 435/6 |
| 2011/0183321 A1 | 7/2011 | Williams et al. | 435/6.1 |
| 2011/0287426 A1 | 11/2011 | Ulmer | 356/436 |
| 2013/0137091 A1 | 5/2013 | Gordon et al. | 435/91.5 |
| 2013/0217596 A1 | 8/2013 | Gordon et al. | 435/6.1 |
| 2013/0316914 A1 | 11/2013 | Gordon et al. | 435/6.1 |

OTHER PUBLICATIONS

PCT International Search Report of International Application No. PCT/US2016/043216 dated Oct. 7, 2016.

\* cited by examiner

*Primary Examiner* — Jezia Riley
(74) *Attorney, Agent, or Firm* — Medlen & Carroll, LLP

(57) ABSTRACT

Modular flow cells, devices with modular flow cells, and methods of sequencing using modular flow cells, as well as systems and kits including modular flow cells, are described, permitting sequencing wherein less than the full capacity for sequencing is desired.

8 Claims, 4 Drawing Sheets

MODULAR FLOW CELLS AND METHODS OF SEQUENCING

FIELD OF THE INVENTION

The invention relates to modular flow cells, devices with modular flow cells, and methods of sequencing using modular flow cells, as well as systems and kits including modular flow cells with other components, including without limitation, reagents, mixtures, data processing steps, algorithms, computer readable media, and computer programs, for determining the identity of nucleic acids in nucleotide sequences using, for example, data obtained from sequencing by synthesis, sequencing by ligation and other nucleic acid sequencing methods. In one embodiment, the present invention provides methods and devices for smaller sequencing projects, i.e. sequencing nucleic acids in smaller batches.

BACKGROUND OF THE INVENTION

Over the past 25 years, the amount of DNA sequence information that has been generated and deposited into Genbank has grown exponentially. Many of the next-generation sequencing technologies use a form of sequencing by synthesis (SBS), wherein specially designed nucleotides and DNA polymerases are used to read the sequence of DNA templates in a controlled manner. Other next-generation sequencing technologies may use native nucleotides and/or polymerases or labeled oligonucleotides and ligation enzymes to determine nucleic acid sequences. To attain high throughput, many millions of such template are used, each being either single or multiple molecules, are arrayed across a surface and their sequence is independently read out and recorded. The desire to perform high throughput sequencing stems from the need for faster processing and reduced costs. However, commercial high throughput systems, while reducing the cost of large scale sequencing (e.g. 100-200 gigabases), make smaller scale sequencing (e.g. 10, 20, 25, etc. gigabases) costly and inconvenient. There is, therefore, a continued need for improved methods and devices for sequencing nucleic acid in order to address the practical day-to-day sequencing work of the average scientist.

SUMMARY OF THE INVENTION

The invention relates to modular flow cells, devices with modular flow cells, and methods of sequencing using modular flow cells, as well as systems and kits including modular flow cells with other components, including without limitation, reagents, mixtures, data processing steps, algorithms, computer readable media, and computer programs, for determining the identity of nucleic acids in nucleotide sequences using, for example, data obtained from sequencing by synthesis, sequencing by ligation and other nucleic acid sequencing methods. In one embodiment, the present invention provides methods and devices for smaller sequencing projects, i.e. sequencing nucleic acids in smaller batches. The concept could be realized by either nesting flow cells or modular flow cells. Modular flow cells permit flexible amounts of sequencing wherein less than the full capacity for sequencing is desired.

At present, most highly parallel commercial sequencers require the user to run an entire, large flow cell, no matter what size the study or how many (or few) separate samples one might need. This is due to current designs which employ a single flow cell or dual flow cells, wherein all reagents and washes occur at a single station for each flow cell and valving is used to change the reagent delivered to the flow cell. This lack of flexibility has a number of unfavorable consequences. First, it means that one must either tolerate the waste and higher costs of smaller sequencing jobs or wait until a number of smaller sequencing jobs can be combined into a larger run. Second, it means that large sequencing projects will be favored (e.g. at a core facility) since they are more cost-effective, causing the average researcher with the smaller project to be excluded or (at best) forced to wait days to weeks before getting access to a shared machine.

In one embodiment, the present invention provides important features in a sequencing system that result in greater flexibility. That is to say, researchers who want to run a relatively small sequencing study (e.g. 10, 20, 25 gigabases) can do so without waiting days to weeks to be "fit" into a larger run. Indeed, researchers can choose the size of their projects and scale their reagent usage accordingly, resulting in cost-effective smaller runs. For example, in one embodiment, prefilled reagent cartridges (or another reagent source) match the flow cell output capacity (whether 25, 50, 75 or 100 GB), thereby allowing for a fixed cost per GB.

In one embodiment, this flexibility is provided by modular flow cells, i.e. flow cells having more than one lane or channel for sequencing, each lane or channel being either active or inactive in a module. In one embodiment, a plurality of modules are pre-assembled together. It is not intended that the present invention be limited to the number of modules; 2, 3, 4, 5, 6, 7, 8, 9, and 10 or more modules can be pre-assembled together. In another embodiment, the modules are inserts that can be introduced into the chamber of the flow cell, each insert providing a lane or channel for performing sequencing. In one embodiment, these inserts are (preferably) both moveable and removeable.

The inactive lanes or channels ("dummy lanes") can be made that way by a variety of approaches, including but not limited to, by not surface modifying them, by not introducing sequencing reagents into them, or by blocking any interaction with sequencing reagents, e.g. with a plug(s) that prevents reagent from reaching the lane. The active lanes are surface modified to contain starting material(s) for sequencing, e.g. attached primer, template or both. Each lane or channel can be associated with its own fluid channel input and output, or they can share a common input and output.

It is not intended that the present invention be limited to the dimensions of the lane or channel. However, the width is between 1 and 5 mm, with the length between 5 and 100 mm; where the lane or channel has depth, it is preferably between 10-300 microns, and more preferably between 10 and 150 microns deep. The dimensions can be adjusted based on the size of the reaction chamber and desired area to be imaged. For example, in one embodiment the size of the reaction chamber or flow cell is dimensioned so that the area to be imaged is less than the size of a standard microscope slide (i.e. less than 75 mm×25 mm) and preferably considerably less (e.g. 35 mm×2.5 mm, or smaller).

It is also not intended that the present invention be limited to particular reagent volumes. However, it is preferred that the reagent volume use for each lane or channel in each module is between 1 and 100 microliters, and more typically between 10 and 40 microliters, and more preferably approximately 20 microliters, in order to reduce costs. In addition, the amount of area that is imaged is reduced (allowing for faster imaging times and less expensive imaging equipment). Thus, rather than continuing to scale up sequencing, the present invention, in one embodiment, takes the approach of sequencing in smaller batches.

These changes also provide advantages in the context of genomic analysis and diagnostic testing, including but not limited to, sequencing of polymorphic areas in the genome that are linked to disease. Rather than using a relatively large single array or chip in a single flow cell, wherein the nucleic acid of a plurality of subjects, including but not limited to human patients, are combined, the present invention contemplates, in one embodiment, using a plurality of modules, where each module contains the nucleic acid of but a single subject, including but not limited to a single human patient. In this manner, the sequencing may be completed faster and more cost effectively as compared to larger flow cell systems.

DESCRIPTION OF THE FIGURES

As noted above, the present invention provides alternatives to using a relatively large single array or chip in a single flow cell. The concept can be realized by either nesting flow cells or modular flow cells. FIG. 1A simply provides an example of three such flow cells. Each flow cell or array can have a dedicated reagent input that is not shared. Alternatively, as shown in FIG. 1A, the small flow cell or array (A) has an input conduit (1), the larger flow cell or array (B) has an input conduit (2), and the largest flow cell or array (C) has an input conduit (3), each coming from a shared reagent source or reservoir (4), where control over reagent input is achieved by a switching valve (5) or other mechanism. Of course, other connection schemes (e.g. T-like connector) can be employed.

FIG. 1B shows an embodiment with as many as four active lanes (A, B, C, and D); however, an active lane (e.g. D) is modular and can be substituted (see arrows) with a dummy lane (stripes) insert or adapter. Again, the lanes or channels of the various modules might share a single reagent source (as shown in FIG. 1B) that is controlled with a switching valve (5) to provide the desired reagent input through conduits (1, 2, 3 and 4) connecting to the modules (A, B, C and D). On the other hand, each lane could be associated with an individual, dedicated (unshared) reagent input. Of course, other connection schemes (e.g. T-like connector) can be employed.

Flow of reagent can be achieved in a number of ways, including (but not limited to) through the use of syringe pumps (6, 7, 8 and 9).

Figure 1A:
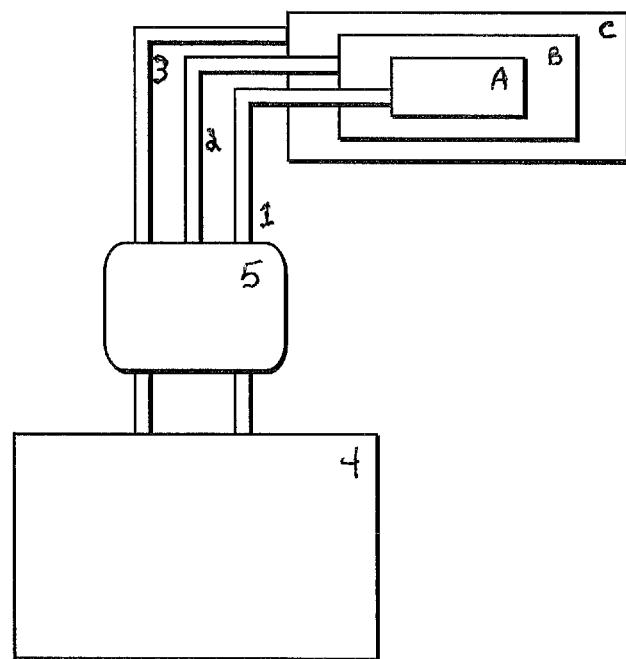
FIG. 1A schematically shows one embodiment of a nesting scheme, wherein a small flow cell or array (A) is nested within a larger flow cell or array (B) which is in turn nested within yet a larger flow cell or array (C). The user chooses which size of flow cell or array to employ depending on the size of the sequencing run or project, and that area receives reagent and is imaged. Of course, other geometries and additional flow cells (whether larger or smaller) can be used.
Figure 1B:
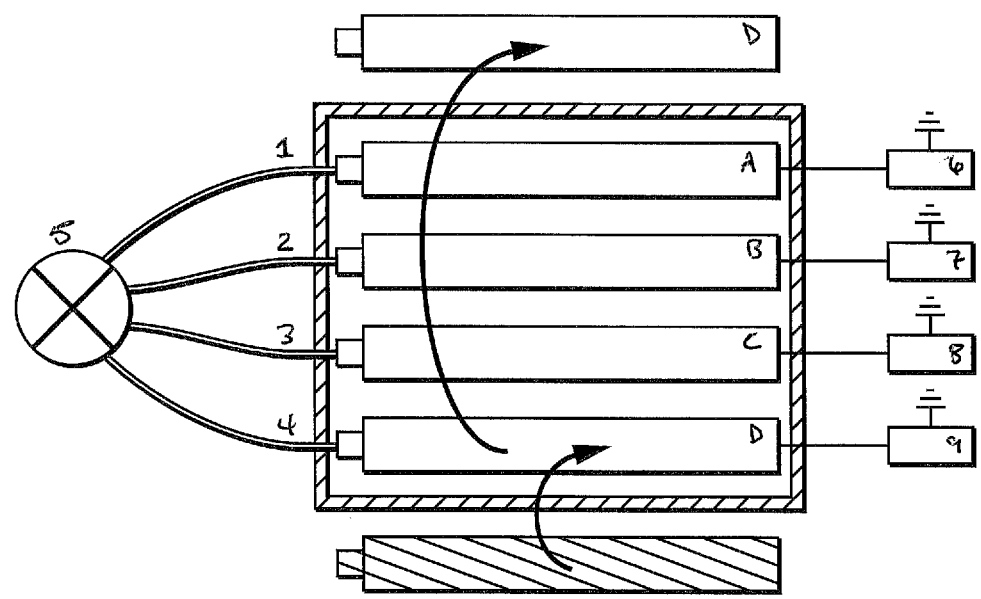
FIG. 1B schematically shows one embodiment of a modular flow cell concept. The modular flow cell concept provides for flexible outputs. While the maximum output might be 100 gigabases ("GB"), the more common or desirable output range would be less than 100 GB, e.g. 10, 20, 25, 50 or 75 GB. In practical terms it would make sense to "divide" the flow cell into equal increments, say 25, 50, 75 and 100 GB. The concept could be realized by either nesting flow cells (as shown in FIG. 1A) or modular flow cells (as shown in FIG. 1B). In one embodiment, modular flow cells have lanes that are either active (surface modified with DNA, e.g. primers, template or both) or inactive (e.g. dummies with no DNA, or dummies with DNA, but no reagent flow). In a preferred embodiment, the flow cell cartridge or other reagent source has the capability to accommodate varying numbers of active (shown in FIG. 1B as clear) and dummy lanes (shown in FIG. 1B with stripes).
Figure 1C:
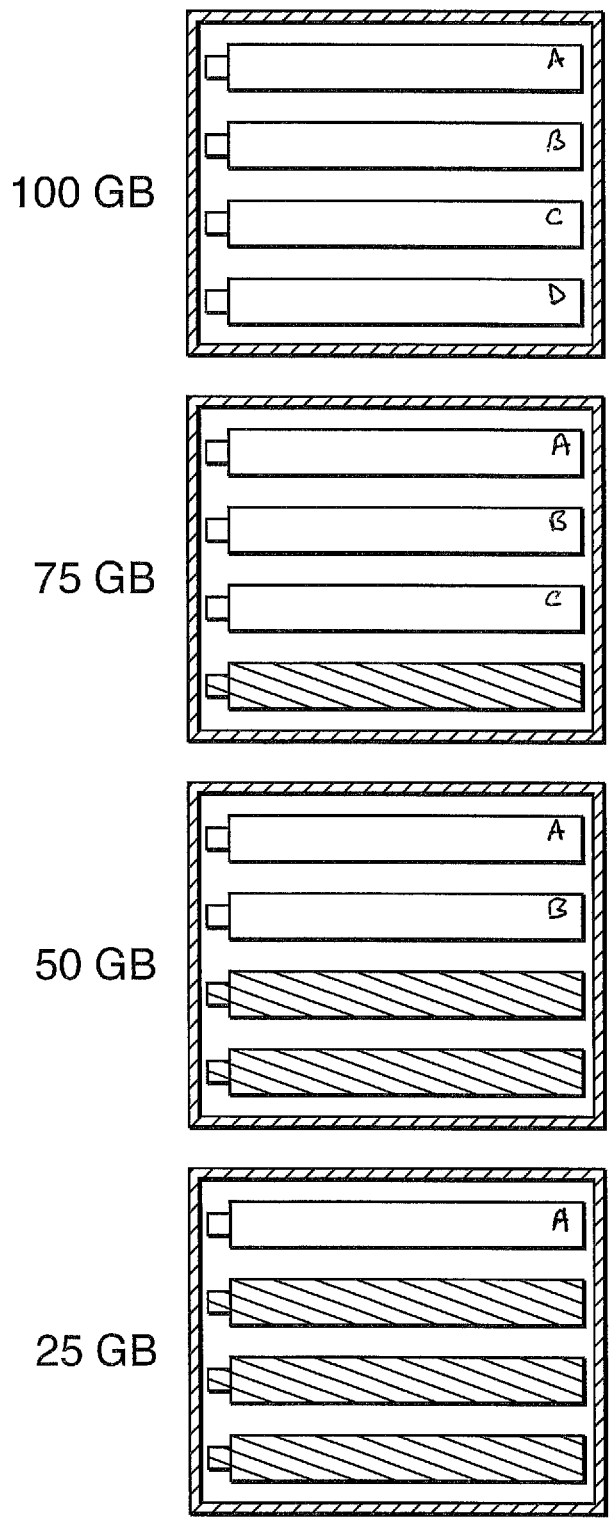

FIG. 1C schematically shows an embodiment with as few as one active lane (A), i.e. embodiments with 0, 1, 2 and 3 dummy lanes (stripes). In one embodiment, prefilled reagent cartridges (or another reagent source) match the flow cell output capacity (whether 25, 50, 75 or 100 GB), thereby allowing for a fixed cost per GB. For example, where there is only one active lane (25 GB), the amount of reagent is reduced (e.g. to one fourth of what was used for 100 GB) to match the needs for that one lane.

Figure 2:
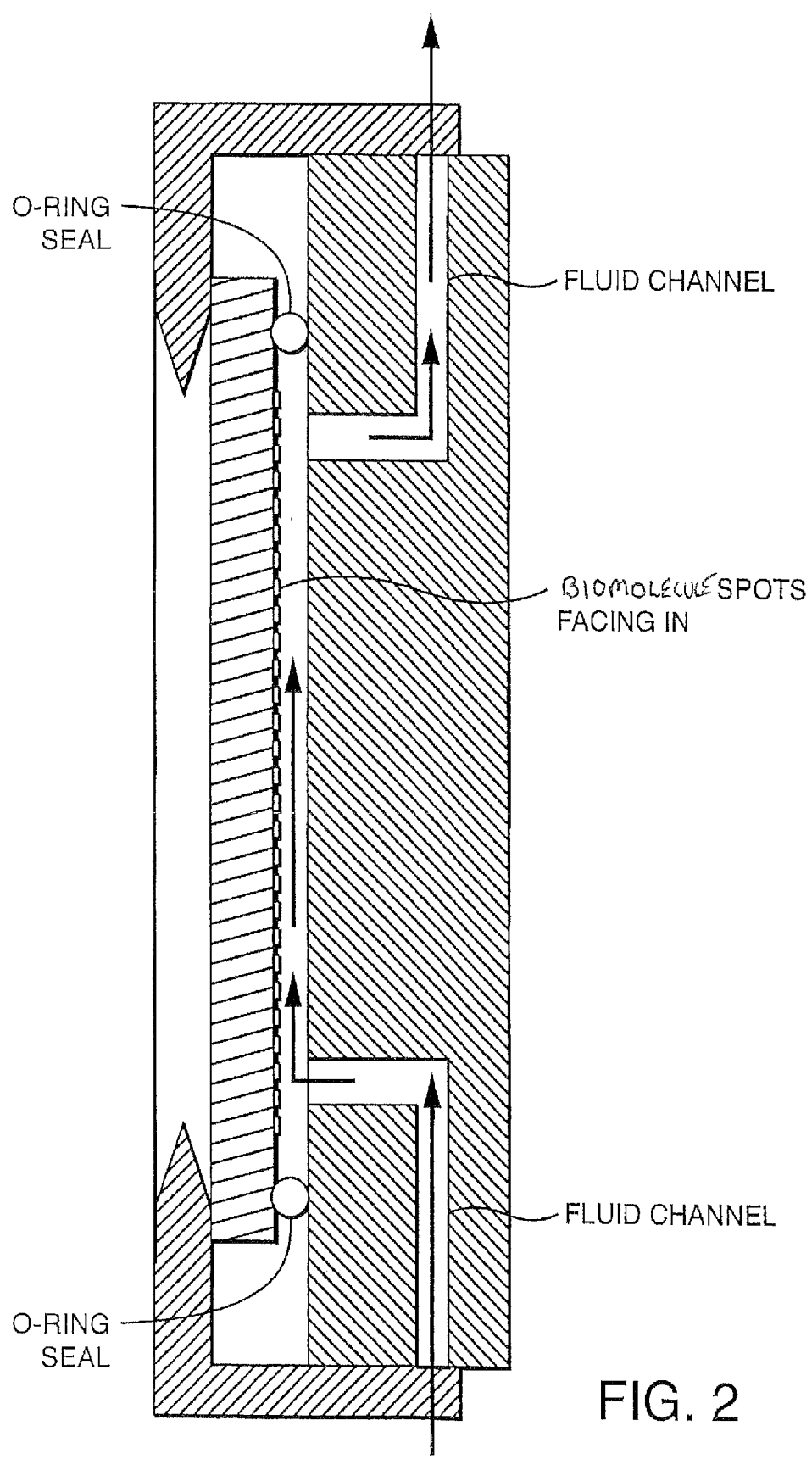

FIG. 2 schematically shows one embodiment of a single module of a modular flow cell in a two dimensional drawing (side view). In one embodiment, the module comprises a lane or channel having a surface. In one embodiment, the surface is modified, e.g. with one or more starting reagents for sequencing (e.g. attached primers in spots on the surface). The surface can be modified with other molecules or biomolecules as well, e.g. anchoring molecules. While the spots are shown on the top surface, they could be on the lower surface of the channel (or on both surfaces). In some embodiments, the spots may contain beads, i.e. the surface of the beads are modified with primers, template or both. In general, the biomolecules (e.g. primers, template or both) are positioned in a fluid channel such that solutions of buffers and sequencing reagents can be introduced over the surface under conditions whereby reactions and/or washing can be achieved. The arrows show one preferred direction of fluid flow, with entrance (input) and exit (output) ports, as well as one preferred method of sealing (O-ring seal). The input and output ports are attached to reagent sources of a fluidic system using fluid tubing connections. Optionally, each module can have a heat source, e.g. a cartridge heater. Importantly, each module can be attached to another module (or simply positioned side by side in a carrier or holder) prior to sequencing, e.g. pre-assembled into a modular flow cell.

Figure 3:
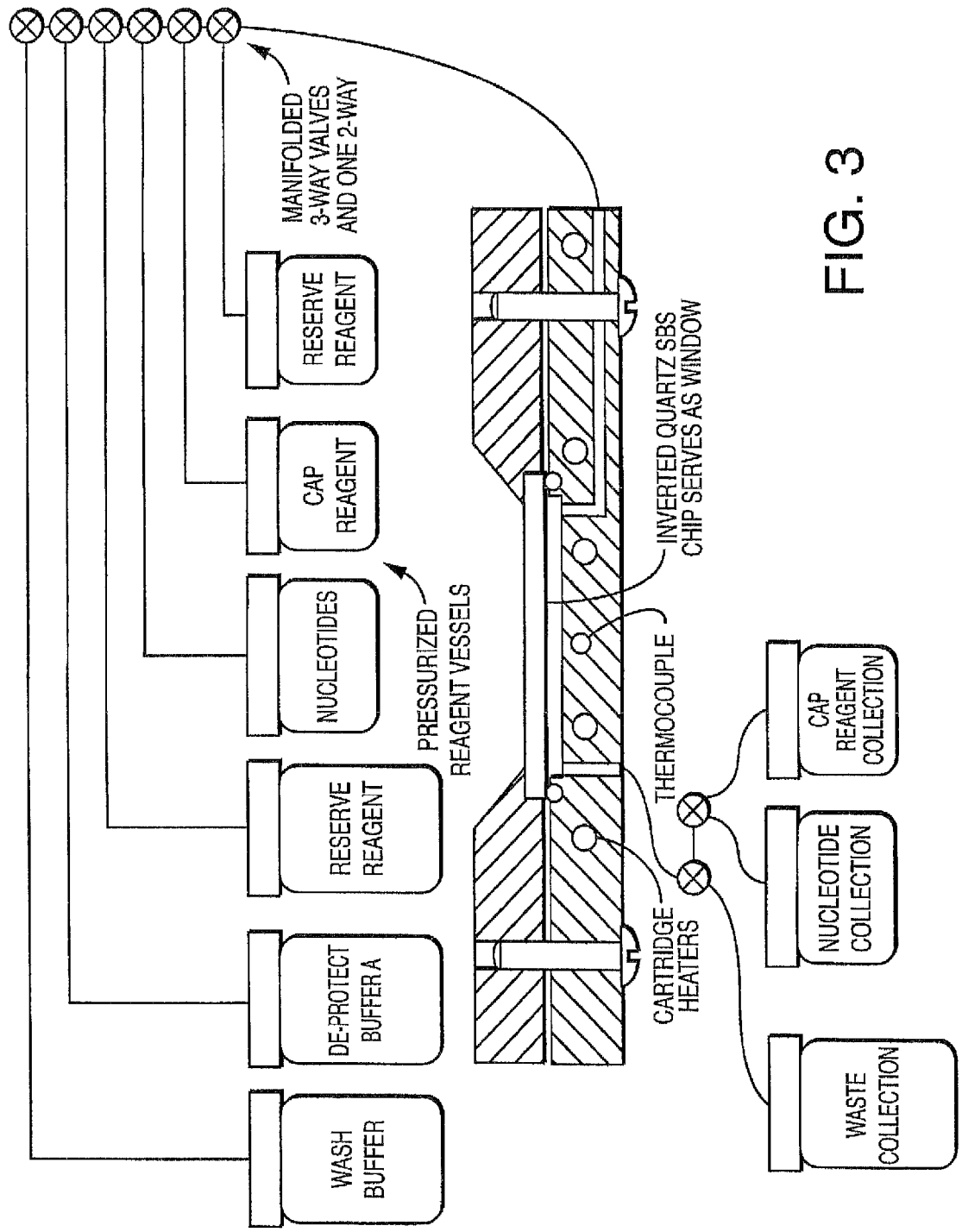

FIG. 3 schematically shows one embodiment of a fluidics system, comprising a variety of illustrative reagent and buffer reservoirs in communication (via tubing or other channeling into a manifold comprising valves) with one embodiment of a flow cell module (comprising a side entrance port and one or more optional heaters), wherein the array or chip is inverted and the exit port is on the bottom, thereby permitting the fluid channel to be drained at least in part by gravity so that waste can be readily collected into a reservoir. The fluidic system delivers the nucleic acids, enzymes, buffers, etc. that are required to produce the fluorescent signals required for each sequencing step, then the required reagents are delivered to remove the fluorescent signals in preparation for the next cycle. Measurement by the detector occurs between these two steps. The sequencing, imaging and analysis are described in more detail in U.S. Pat. No. 8,612,161, hereby incorporated by reference. In one embodiment, the individual modules or the modular flow cell comprise a transparent portion or "window" for imaging.

The heaters can be useful for another embodiment, where different processes are taking place in two different modules of a flow cell. In this "split flow cell" concept, a portion of flow cell (e.g. one or two modules) is imaged while a second portion (e.g. one or two modules) is undergoing chemistry. A thermal insulation is provided so that imaged portion and chemistry portion have independent temperature controls, for example Peltier units.

DESCRIPTION OF PREFERRED EMBODIMENTS

In one embodiment, the present invention contemplates carrying out nucleotide incorporation in a device, including automated devices comprising modular flow cells. Solutions comprising various combinations of biomolecules are contemplated; such solutions can be, in one embodiment, conveniently stored in reservoirs which are in fluid communication with the modular flow cells. A series of steps can be carried out to introduce these solutions (and the reagents they contain) into the reaction chamber (e.g. by valving) to carry out the reaction(s).

Thus, in one embodiment, the present invention contemplates a method of incorporating labeled nucleotides into nucleic acid, comprising: a) providing i) a modular flow cell comprising a plurality of modules, each module comprising biomolecules (e.g. primer, nucleic acid template or both) bound to a surface (e.g. of a lane, fluidic channel, or bead in a lane or channel), said plurality of modules sharing an input and output port, ii) a first solution comprising polymerase and a plurality of nucleotide analogues wherein at least one nucleotide analogue is labeled with a unique label (the other nucleotide analogues may or may not be labeled) and each nucleotide contains a removable chemical moiety capping the 3'-OH group, iii) a second solution comprising a cleaving agent; b) introducing said first solution into at least one module of said plurality of modules under conditions wherein a first nucleotide analogue is incorporated by said polymerase (and optionally, not introducing said first solution into all of the modules); c) detecting the label of the incorporated nucleotide analogue; and d) introducing said second solution into said at least one module under conditions such that the chemical moiety of the incorporated nucleotide analogue capping the 3'-OH group is removed by said cleaving agent. In one embodiment of this method, each module comprises a fluidic channel and the fluidic channel of at least one module is blocked so that no solutions enter said blocked fluidic channel. In one embodiment, the fluidic channel of said one module is blocked with a plug.

In one embodiment, the present invention contemplates a method of incorporating labeled nucleotides into nucleic acid, comprising: a) providing i) a modular flow cell comprising a plurality of modules, each module comprising biomolecules (e.g. primer, nucleic acid template or both) bound to a surface of a fluidic channel, each fluidic channel having a separate input and output port, ii) a first solution comprising polymerase and a plurality of nucleotide analogues wherein at least one nucleotide analogue is labeled with a unique label (again, the other nucleotides may or may not be labeled) and contains a removable chemical moiety capping the 3'-OH group, iii) a second solution comprising a cleaving agent; b) introducing said first solution into at least one module of said plurality of modules under conditions wherein a first nucleotide analogue is incorporated by said polymerase (and optionally, not introducing said first solution into all of the modules); c) detecting the label of the incorporated nucleotide analogue; and d) introducing said second solution into said at least one module under conditions such that the chemical moiety of the incorporated nucleotide analogue capping the 3'-OH group is removed by said cleaving agent. In one embodiment of this method, each module comprises a fluidic channel and the fluidic channel of at least one module is blocked so that no solutions enter said blocked fluidic channel. In one embodiment, the fluidic channel of said one module is blocked with a plug.

In another embodiment, the present invention contemplates a method of incorporating labeled nucleotides into nucleic acid, comprising: a) providing i) a modular flow cell comprising four modules, at least one (and up to three) of which comprise biomolecules (e.g. primer, nucleic acid template or both) bound to a surface of a fluidic channel; ii) a first solution comprising polymerase and a plurality of nucleotide analogues wherein each nucleotide analogue is labeled with a unique label and contains a removable chemical moiety capping the 3'-OH group, iii) a second solution comprising a cleaving agent; b) introducing said first solution into said four modules (or at least the one with the biomolecules) under conditions wherein a first nucleotide analogue is incorporated by said polymerase; c) detecting the label of the incorporated nucleotide analogue; and d) introducing said second solution into said at least one module under conditions such that the chemical moiety of the incorporated nucleotide analogue capping the 3'-OH group is removed by said cleaving agent. In one embodiment of this method, at least one module (and up to three modules) comprises no biomolecules in the fluidic channel, i.e. the channel lacks the starting materials (e.g. primer, templates, or both) for sequencing and no sequencing takes place.

In yet another embodiment, the present invention contemplates a method for carrying out process steps for nucleic acid sequencing, comprising: a) providing i) a modular flow cell comprising first and second modules, each module comprising a fluidic channel, ii) nucleic acid to be sequenced, iii) nucleic acid sequencing reagents, and iv) a camera; and b) introducing said nucleic acid to be sequenced and said nucleic acid sequencing reagents into said first and second modules of said modular flow cell under conditions such that, while said first module is undergoing one or more reaction steps, said second module is being scanned and imaged with said camera.

In one embodiment, the present invention contemplates kits comprising modular flow cells together with other components, including without limitation, reagents, and reagent mixtures. The kits can be used together with automated devices for determining the identity of nucleic acids in nucleotide sequences using, for example, sequencing by synthesis, sequencing by ligation and other nucleic acid sequencing methods.

The invention claimed is:

1. A method of incorporating labeled nucleotides into nucleic acid, comprising:
   a) providing
      i) a modular flow cell comprising a plurality of modules, wherein said modules are moveable and removable inserts, each module comprising biomolecules bound to a surface of a lane or fluidic channel, said plurality of modules sharing an input and output port, wherein each module comprises a fluidic channel and the fluidic channel of one module is blocked so that no solutions enter said blocked fluidic channel, and
      ii) a solution comprising polymerase and a plurality of nucleotide analogues wherein at least one nucleotide analogue is labeled with a unique label;
   b) introducing said solution into at least one module of said plurality of modules under conditions wherein a first nucleotide analogue is incorporated by said polymerase; and
   c) detecting the label of the incorporated nucleotide analogue.

2. The method of claim 1, wherein the fluidic channel of said one module is blocked with a plug.

3. The method of claim 1, wherein said biomolecules comprise primers for sequencing.

4. A method of incorporating labeled nucleotides into nucleic acid, comprising:
   a) providing
      i) a modular flow cell comprising a plurality of modules, wherein said modules are moveable and removable inserts, each module comprising biomolecules bound to a surface of a fluidic channel, each fluidic channel having a separate input and output port, wherein the fluidic channel of one module is blocked so that no solutions enter said blocked fluidic channel, and
      ii) a solution comprising polymerase and a plurality of nucleotide analogues wherein at least one nucleotide analogue is labeled with a unique label;
   b) introducing said solution into at least one module of said plurality of modules under conditions wherein a first nucleotide analogue is incorporated by said polymerase; and
   c) detecting the label of the incorporated nucleotide analogue.

5. The method of claim 4, wherein the fluidic channel of said one module is blocked with a plug.

6. The method of claim 4, wherein said biomolecules comprise primers.

7. A method of incorporating labeled nucleotides into nucleic acid, comprising:
   a) providing
      i) a modular flow cell comprising four modules, wherein said modules are moveable and removable inserts, at least one of which comprise biomolecules bound to a surface of a fluidic channel, wherein one module comprises no biomolecules in the fluidic channel, and no sequencing takes place in that channel; and
      ii) a solution comprising polymerase and a plurality of nucleotide analogues wherein each nucleotide analogue is labeled;
   b) introducing said solution into said four modules under conditions wherein a first nucleotide analogue is incorporated by said polymerase;
   c) detecting the label of the incorporated nucleotide analogue.

8. The method of claim 7, wherein said biomolecules comprise primers for sequencing.

* * * * *